Figure 1:
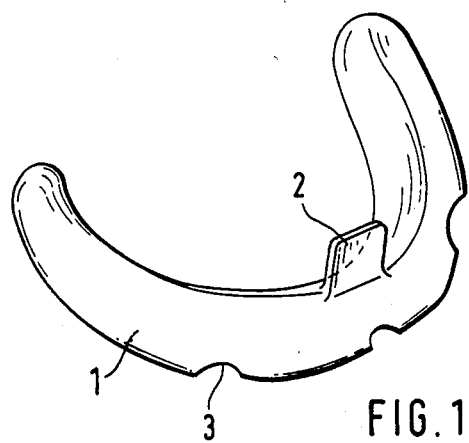

United States Patent [19]

von Nostitz

[11] Patent Number: 4,569,342

[45] Date of Patent: Feb. 11, 1986

[54] DENTAL IMPRESSION TRAY AND PROCESS FOR THE USE THEREOF

[76] Inventor: Frauke H. F. von Nostitz, Allescherstrasse 45, D-8000 Munich 71, Fed. Rep. of Germany

[21] Appl. No.: 541,318

[22] Filed: Oct. 13, 1983

[30] Foreign Application Priority Data

Oct. 20, 1982 [DE] Fed. Rep. of Germany ....... 3238816

[51] Int. Cl.[4] .............................................. A61F 5/56
[52] U.S. Cl. ...................................... 128/136; 433/48
[58] Field of Search ...................... 433/48, 37, 39, 42, 433/6; 128/136

[56] References Cited

U.S. PATENT DOCUMENTS

| | | | |
|---|---|---|---|
| 3,379,193 | 4/1968 | Monaghan | 433/6 |
| 3,407,808 | 10/1968 | Baldwin | 128/136 |
| 3,411,501 | 11/1968 | Greenberg | 128/136 |
| 3,864,832 | 2/1975 | Carlson | 128/136 |
| 4,016,650 | 4/1977 | Leusner et al. | 433/42 |
| 4,227,877 | 10/1980 | Tureaud et al. | 433/37 |

*Primary Examiner*—Robert Peshock
*Attorney, Agent, or Firm*—James J. Ralabate

[57] ABSTRACT

A dental impression tray has approximately the form of the upper or lower biting surfaces and is made of thermoplastics material. The dental impression tray may be used to produce a functional impression of the upper or lower biting surfaces, including an occlusal impression, and is further suitable, in combination with a suitable lining material, as a dental guard for sportsmen.

9 Claims, 2 Drawing Figures

DENTAL IMPRESSION TRAY AND PROCESS FOR THE USE THEREOF

This invention relates to a dental impression tray and to processes using the tray. The invention is applicable to the production of a functional model of the upper and/or lower teeth and gum area (hereinafter referred to as "biting surfaces"), including an occlusion impression, as well as for the production of a dental guard.

When using the conventional processes it is first necessary, when making a denture or a partial denture, to produce a rough, negative topological impression. This is taken with the assistance of a standard perforated metal or plastics tray, wherein for the impression material alginate, palgate, etc. are used.

Then the topological impression is used to form a cast using hard plaster, which produces a positive topological model, which reflects the rough topology found in the mouth or on the biting surfaces of the patient, i.e. existing or absent teeth, the shape of the jaw crest and the mucous membranes, irregularities, etc.

Now a negative topological tray, the so-called "functional tray", is produced from the positive model. This tray usually consists of plastics and is made individually according to the configuration of the topological impression.

With the aid of the functional tray and using special molding materials, e.g. sila-plast or sila-soft, a precise topological or "functional" impression is then taken in the patient's mouth, which reflects the detail of the biting surfaces including that of the movable parts, such as the mucous membranes which move during their functions, such as when laughing, talking, chewing, etc.

The functional impression is then used to produce a cast with a special hard plaster, which produces a precise topological or "functional" model, which is a reproduction which is truer to pattern than the initial rough topological model, especially with respect to the mucous membranes, frenulum, etc. during their movements.

Then an occlusion mold or bite impression is made in the patient's mouth on the functional model by the application of an occlusion wall or layer to the model onto which the patient bites. This impression reflects the occlusal planes, the position of the biting surfaces in relation to each other, the center line of the face and the laughing line.

The final denture or plate is then produced on the basis of the bite impression and functional model.

Thus, according to the above-described previously used process, at least two sessions of the patient with the dentist are necessary to arrive at a functional model including the occlusal impression. Moreover, the production of the rough topological model and the precise functional model gives rise to excessive labor and material costs.

It is desirable to simplify the making of the funtional model for the production of a denture, or of a partial denture, so that the functional model including the occlusal mold is made with optimal reproduction of details at a lower cost in terms of time and money.

In addition, it is desirable to make available to sportsmen, especially to boxers, soccer and rugby football players, a dental guard which can be made quickly, and if possible by the sportsman himself, by simple means, and which is also individually adapted to the dental topology concerned.

A dental guard is already known, but the conventional method uses a tray manufactured in a laborious deep drawing process and, as soft intermediate material between the tray and the biting surfaces, a silicon, a soft hot polymer or the like is used. These lining materials have the disadvantage that they very rapidly become unattractive and moreover they do not form any surface connection with the tray. Furthermore, the long processing time of these lining materials is a disadvantage.

Thus, there is a need for a dental guard which preferably can be accurately adapted to the teeth by the sportsman himself by self-treatment, which can be made simply and with low costs, and which enters into an ideal surface connection with the lining material after only a brief processing time, so that together with said lining material, by the combination of the relatively hard tray material with the soft molding material, it produces a dental guard for the respective lower or upper row of teeth and also creates excellent protection in counter-occlusion or in co-occlusion to the opposite row of teeth.

An object of the present invention is to provide a dental impression tray by means of which a precise functional impression of the upper or lower biting surfaces, partially or fully provided with teeth, can be produced. The term "dental impression tray" according to the invention comprises a usual dental impression tray as well as a dental functional impression tray.

It is important that this functional model, in combination with a suitable molding material, should ensure a true reflection of the upper or lower biting surfaces as well as the production of an occlusion mold in a simple and economical manner. In addition a dental impression tray is to be provided which, due to its ideal adaptation to the upper or lower biting surfaces and dental situation, forms a dental guard, especially for sportsmen.

The object above is achieved by the invention by means of a dental impression tray, which has approximately the form of the upper or lower biting surfaces and consists of a thermoplastics material.

In particular, a dental impression tray with the features above is produced, which can serve in the production of a precise functional model of the upper or lower biting surfaces as well as of an occlusion mold. Further, the inventive dental impression tray can serve to produce a dental guard, especially for soccer and rugby football players, as well as boxers, etc. Moreover, according to further aspects of the invention, application processes using the inventive dental impression tray are described.

The designation dental impression tray replaces the hitherto usual standard tray for the rough impression and the functional impression tray.

The dental impression tray according to the invention preferably has in the middle of the occlusion area a grip made of a thermoplastics material which, after fitting to the jaw or dental conditions, is removed by being cut or sawn off.

The dental impression tray according to the invention differs from the trays conventionally used in dentures in that it is made in a form which is approximated to the form of the lower or upper biting surfaces and consists of a thermoplastics material which becomes soft or flexible at a temperature in the range from 50° C. to 80° C. so that it can be adapted to the dental conditions or biting surfaces of the patient in a simple manner to form a functional tray which can be used for all applications of the conventional functional tray.

Furthermore, the conventional functional tray has to be made firstly via a situation impression and then via the situation model produced thereby.

The approximate adaptation of the impression tray according to the invention to the biting surfaces makes it possible, when using a suitable material, to use the impression tray directly for the production of a functional tray. In practice, this means that the dentist will have available varying sizes of impression trays, and that he can then select the one suitable for the patient.

The dental impression tray according to the invention is made of a thermoplastics material. In this way it is possible to bring the material of the impression tray, which is rigid at normal temperatures, into a plastic state by raising the temperature, e.g. by immersion in a hot water bath, which makes possible an exact reproduction of the biting surfaces of the patient.

The thermoplastics material from which the dental impression tray of the invention is made is preferably an acrylate plastics material. Particularly suitable are the plastics which are derived from acrylic or methacrylic acid. Especial preference is given to the use of methylmethacrylate.

Within the scope of the invention the dental impression tray can also be made from an acrylic or methacrylic ester with 6 to 10 C-atoms or from a mixture thereof. It is also possible to use the low esters of the named acrylic or methacrylic acid, such as ester derivates with more than 10 C-atoms, which are suitable for the production of the dental impression tray according to the invention. Specially preferred material within the scope of the invention for the production of the dental impression tray is provided by acrylic and methacrylic acid hexyl ester, while the hexyl component can also be of a cyclical type. But the t-butyl esters or epoxypropyl esters of acrylic or methacrylic acid are also suitable.

It is particularly advantageous to choose an acrylic or methacrylic acid ester which becomes soft or flexible at a temperature in the range from 50° C. to 80° C., preferably in the range from 60° C. to 70° C.

Within the scope of the invention, the use of methylmethacrylate (MMA) is also suitable as the thermoplastics material.

One preferred embodiment of the invention consists of the use of acrylic or methacrylic acid esters with a total of 6 to 10 C-atoms or a mixture thereof, in the absence of methylmethacrylate.

The above-named plastics from which the dental impression tray is made are also distinguished inter alia by the fact that they do not possess any unpleasant taste or smell.

To attain not only good flexibility, but also toughness of the chosen ester components, it is often advisable to insert a certain share of a softener. Suitable softeners are for example alkyl sulfonic acid esters of phenol (e.g. "Mesamol" from Bayer).

In addition, shares of mixed polymer, filler, stabiliser, dyes and other known adjuvants may be present.

The dental impression tray of the invention may be distinguished moreover by the fact that its interior, i.e. the gingival side and/or the compress side, is provided with a roughened surface. In addition, the dental impression tray of the invention may have on its rim material recesses, which allow a better adaptation of the tray to the biting surfaces.

The dental impression tray according to the invention preferably has a wall thickness of from 0.3 to 2.5 mm, preferably from 0.5 to 2.5 mm. It has been found that a wall thickness of more than 2.5 mm makes the reproduction of an impression true to detail more difficult.

The same dental impression tray which is used for the production of a functional model can also be used, after adaptation to the upper or lower row of teeth, as a dental guard.

When the dental impression tray of the invention is used to make a dental guard, it is adapted to the upper or lower row of teeth while the edges or the lateral surfaces which may be too high can be cut off by using scissors.

The dental impression tray which is used for the production of a dental guard can be fitted with a grip made of thermoplastics material for greater ease in handling.

Preferably the dental impression tray used for the production of a dental guard has apertures in the center of the occlusion area, which after provision of a lining material, can be penetrated by the latter in order to form a preferably soft dental guard in counter-occlusion to the opposite row of teeth.

The dental guard using the dental impression tray according to the invention can be applied both by the dentist and by the sportsman himself together with the soft molding material.

Figure 2:
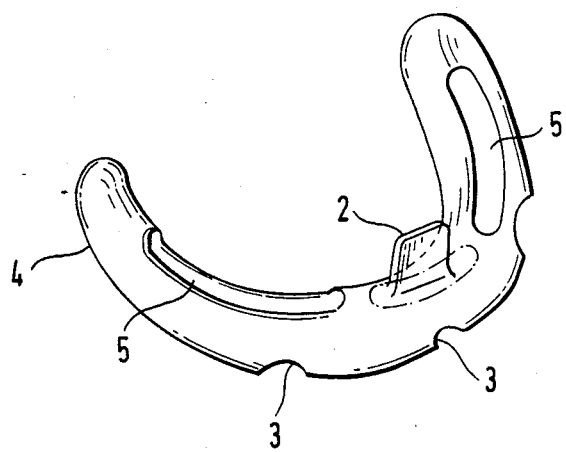

For a better understanding of the invention, and to show how the same may be carried into effect, reference will now be made, by way of example, to the accompanying drawing, in which:

FIGS. 1 and 2 show perspective illustrations of dental impression trays, the embodiment in FIG. 1 being especially suitable for the production of a functional model of the upper or the lower biting surfaces, whereas the embodiment in FIG. 2 is preferably used for the production of a dental guard.

Referring first of all to FIG. 1, the illustrated dental impression tray 1 consists of a generally U-shaped channel member of thermoplastics material. By the term "channel member" is meant that all cross-sections perpendicular to the U-shaped center line of the member will have a generally U-shaped form of relatively thin wall thickness. The wall thickness is preferably in the range of from 0.3 to 2.5 mm, most preferably from 0.5 to 2.5 mm. The non-visible side of the impression tray, i.e. the gingival side, may be provided with a roughened surface for improved adhesion. On its outer rim, the impression tray is provided with three recesses 3 which allow easier adaptation of the tray to the biting surfaces of a patient. On the upper surface of the tray approximately centrally thereof there is preferably provided a grip member 2 also made of thermoplastics material and preferably integral with the remainder of the tray. It will be understood that the overall U-shape of the tray and the concave lower surface are intended to allow the tray to be inserted over the lower or upper tooth crest or biting surfaces of a patient.

Coming now to FIG. 2, this shows a tray 4 which is for the most part similar to that of FIG. 1 and is provided with the stem-type grip or holder 2. In addition to the features shown in FIG. 1, this tray is provided with apertures 5 on the upper rim or occlusion track of the tray which can be filled with soft plastics material before the tray is applied to the teeth. This embodiment is particularly suitable for the formation of a dental guard for sportsmen. Before the tray can actually be used by a sportsman, the grip member 2 will of course have to be removed and it may in fact be completely unnecessary to provide this grip. Where it is provided, this grip, which also consists of thermoplastics material, can either be pressed back to the rear when the tray is in its plastic condition or it can be cut or sawn off.

The impression tray of FIG. 1 may be used in a process for the production of a functional model of partly or fully-toothed lower or upper biting surfaces, as well as of an occlusion mold. Firstly, the impression tray 1 is softened by immersion in warm water at from 50° C. to 80° C. and then, by light pressure is adapted to the form of the biting surface for the individual production of a functional tray, the surplus material is removed, and the resultant impression is hardened by cooling. Then, molding material is poured into the tray and a functional impression is taken, from which a functional model is made. If an occlusal wall or layer is provided on the functional tray, an occlusion impression can be formed, preferably using the known Schreinemaker process.

If filler material is poured into the functional tray and on the tray the occlusal wall or layer is provided, the production of the functional impression and the odontoscopy can be done simultaneously, or at any rate in one sitting even if the tray is adapted and cooled before the occlusal layer is applied.

Depending on the material used as the thermoplastic, the softening of the functional impression tray is carried out by immersion in warm water at from 50° C. to 80° C., preferably at from 60° C. to 70° C.

The impression tray softened in this manner is then fitted by a dentist to the upper or lower biting surfaces of the patient, applying slight pressure in each individual case. If this is desired, for better adhesion of the impression tray, an adhesive can be used.

Surplus material is removed with a suitable device, e.g. with scissors or with a saw, in a simple manner. The functional tray formed in this way, which is in every respect of value at least equal to the old conventional functional tray, can be hardened by careful cooling, e.g. using cold air or a cold spray. It is also possible to harden the functional tray by immersing it in cold water.

The functional tray thus formed, due to its material used according to the invention, now possesses its optimal stability, and does not have to be reinforced by means of inserts.

Then a suitable molding material, such as is known in dentistry, is poured into the tray, and a functional impression is taken. Using the functional impression, a functional model can now be produced for the production of a complete or partial denture.

For the production of an occlusal mold, an occlusal wall or layer, preferably of wax, is fixed on the impression tray if necessary after being cooled and after solidification, and the occlusal mold impression is made.

According to another variant, the occlusal mold impression can be made simultaneously when producing the functional impression. This process is described in the specialist literature as the molding method according to Schreinemaker.

Because of the elimination of various working steps, the possibilities for errors or subsequent influences which may arise due to transport or when casting some impressions are reduced with the aid of the dental impression tray of the invention, so that a perceptibly greater model precision is attainable than was the case with the previously known processes.

Using the dental impression tray it is possible with optimum execution of the work, to eliminate the following steps: formation of a rough topological impression, production of a rough topological model, the production of a functional tray on the rough model and the manufacture of the occlusal mold.

The dental impression tray is especially suitable for the true-to-form and simple production of a functional model. In addition, by its use, a significant cost saving is achieved.

The tray 4 of FIG. 2 may be applied to a process for the production of a dental guard, especially for sportsmen. The dental impression tray 4 is softened by immersion in warm water at from 50° C. to 80° C., preferably at 70° C., and then is fitted by slight pressure onto the upper or lower row of teeth. Excess material may be removed using scissors or a saw if necessary. The resultant individual functional tray is hardened by cooling.

In the next process step, molding or lining material is poured into the tray and the latter is again pressed onto the upper or lower row of teeth, whereupon the molding material is allowed to polymerize. It then forms, in combination with the relatively hard tray material, a soft buffer substance between the tray and the teeth.

In this process step, molding material partially penetrates into and through the apertures 5 in the occlusal track of the tray, so that these recesses are filled out by the soft plastics molding material. The latter, which is also relatively soft after polymerization, forms a soft buffer zone in the counter-occlusion to the opposite row of teeth.

It is preferable to use a molding material which is fully polymerized after about 15 minutes. Especially preferred is the use of a cold polymer, such as is described below. A special advantage of the molding material described below is that it forms a homogenous compound with the tray, is not unattractive, requires a relatively short processing time of from 10 to 15 minutes, and has almost no shrinkage.

The preferred molding material which is used in combination with the dental impression tray used as the dental guard consists of a self-hardening substance based on monomers and polymers or mixed polymers of acrylic and/or methacrylic acid esters. The monomer ester components have as least a proportion of an acrylic and/or methacrylic acid ester having 6 to 10 C-atoms, the polymer proportion amounts to 10 to 70% by weight, based on the total composition, and contains 0.1 to 10% by weight of a stearate, oxystearate, palmitate, montanate, oleate or ricinoleate of metals (not being heavy metals), as well as optionally an additive of jojoba oil, apart from the usual hardeners and accelerators.

It is particularly preferable if the above-named monomer components either do not contain any substantial share of methyl ester of acrylic acid or methacrylic acid, or are free thereof.

In the molding material described above, preferably a metal soap is used which is a calcium and/or a magnesium stearate.

Additionally, it is an advantage when the molding material as the monomer acrylic and/or methacrylic ester is a t-butyl ester, epoxypropyl ester and/or hexyl ester or a mixture thereof.

The monomer acrylic or methacrylic acid ester, which serves to dissolve or to disperse the polymer share of the molding material, is at least partially effective as a cross-linking agent. It is advantageous that the cross-linking agent is an olefinic dimethacrylate and/or a (poly)-ethyleneglycoldimethacrylate, which is added to the monomer (meth)acrylate or exclusively constitutes the monomer share.

The above-described molding material consists of a powder and a liquid system. The powder system can comprise the above-named polymers, fillers, metal soaps, and peroxide. The liquid system comprises monomer acrylate, softener, accelerator as well as optionally an additive of jojoba oil.

The additive of jojoba oil is in the range of from 0.1 to 10% by weight based on the total weight of the molding substance. Preferably the proportion of jojoba oil amounts to 0.2 to 1% by weight.

The inclusion of jojoba oil or of derivates thereof in the molding substance is advantageous in that it facilitates the processability of the substance, in that it functions as a softener and improves the viscosity of the substance. This advantage is also found after the polymerization of the substance. A further advantage in adding jojoba oil to the molding substance is that it increases the hardness. This is of particular value in the area of the pressure points.

The production of the above-named preferred molding material is effected advantageously in that to a solution, suspension or paste of monomer and (co)-polymer (meth)acrylate are added, the metal soap as well as optionally the jojoba oil, before or after the addition of the accelerator and optionally the cross-linking agent.

Below are described two embodiments of the dental impression tray according to the invention.

EMBODIMENT EXAMPLE 1

A dental impression tray according to the invention made of methacrylic hexyl ester and having approximately the form of the lower biting surfaces of the patient, is placed in warm water for two minutes at 70° C.

The previously hard consistency of the tray material becomes soft and plastic and can be individually adapted in this form to the shape of the biting surfaces. Surplus plastics material is if necessary removed with scissors or with a saw. For immediate cooling and hardening, the resulting functional tray, now individually adapted to the lower biting surfaces, is immersed in cold water for 30 seconds. If there is still any surplus material on the functional tray, it can now be removed.

As the molding material, Sila-plast (Bayer AG, Leverkusen) is now poured into the functional tray and a functional impression is taken in the mouth of the patient.

Then the functional impression is used to form a casting using specially hard plaster, which produces the functional model.

To produce an occlusal mold the functional tray formed as described above is used. On it an occlusal wall made of wax is secured, and in the mouth of the patient an occlusal impression is taken.

EMBODIMENT EXAMPLE 2

A dental impression tray according to FIG. 2 and made of methacrylic hexyl ester is heated by immersion in warm water at 70° C. and is thereby made flexible. By adaptation to the upper or lower row of teeth an impression is formed of the existing dental and biting surface conditions. Surplus rims or lateral areas may be removed if necessary by cutting with scissors. Then a mixed impression material (lining material) is applied, composed of 40% by weight of polymer acrylate, based on the total composition, about 55% by weight of monomer ester component made up of methacrylic acid - hexyl ester, 1% by weight of calcium stearate and optionally 0.5% by weight of jojoba oil, apart from the conventional hardeners and accelerators. This two-component system on an acrylate base polymerizes fully after about 15 minutes as a soft buffer zone between the relatively hard material of the tray and the teeth. This forms a homogenous compound with the tray material. The apertures on the occlusal track of the tray are filled in by the soft plastics material. After about 10 minutes, the lining material is fully polymerized.

This produces a ready-to-use dental guard which can be made by the sportsman himself, and can be used repeatedly.

I claim:

1. Process for the production of a dental guard suitable for sportsmen, comprising the following steps:
   (a) a dental impression tray having a biting area which has been approximately adapted to the upper or lower teeth, has at least one aperture in the biting area, and is made of thermoplastics material, is softened at a temperature in the range from 50° C. to 80° C., and is then individually adapted by light pressure to the upper or lower row of teeth and associated gum area to produce a dental guard, any surplus material is removed, and the individualised tray is hardened by cooling;
   (b) molding material is provided in said tray and it is again pressed onto the upper or the lower row of teeth;
   (c) the molding material is polymerised to form a soft buffer zone between the relatively hard materials of the tray and the teeth and to penetrate partially into and via said at least one aperture to form a soft buffer zone between the tray and the opposite row of teeth.

2. Process according to claim 1 wherein said molding material is a self-hardening substance comprising: a monomer and a (co)polymer of acrylic or methacrylic esters, wherein said monomer has at least one of acrylic and methacrylic esters which possesses from 6 to 10 C-atoms, and the polymer share is 10 to 70% by weight, based on the total composition; and from 0.1 to 1% by weight of a metal soap such as a stearate, oxystearate, palmitate, montanate, oleate, or ricinoleate of a metal, not being a heavy metal; and the usual hardeners and accelerators.

3. Process according to claim 2 wherein jojoba oil is added in a concentration of from 0.1 to 10% by weight, based on the total substance.

4. Process according to claim 2 wherein as the molding material a self-hardening substance is used which contains substantially no methyl ester of acrylic acid or of methacrylic acid.

5. Process according to claim 2 wherein said monomer is at least one of t-butyl ester, epoxypropyl ester, hexyl ester, and a mixture thereof.

6. Process according to claim 2 wherein the monomer acrylic or methacrylic acid ester, which is used for the dissolution or for the dispersion of the polymer share, is at least partially effective as a cross-linking agent.

7. Process according to claim 6 wherein the cross-linking agent is an olefinic dimethylacrylate or a (poly)-ethylenglycoldimethylacrylate which is added to the monomer (meth)acrylate or constitutes the monomer share.

8. Process according to claim 2 wherein said metal soap is added to a solution, suspension or paste of monomer and (co)-polymer (meth)acrylate, either before or after addition of an accelerator.

9. Process according to claim 2 wherein said metal soap comprises calcium or magnesium stearate.

* * * * *